United States Patent
Strickler et al.

(10) Patent No.: US 7,273,941 B2
(45) Date of Patent: Sep. 25, 2007

(54) PROCESS OF PREPARING AN OLEFIN OXIDE FROM OLEFIN AND ORGANIC HYDROPEROXIDE

(75) Inventors: Gary R. Strickler, Midland, MI (US); George J. Quarderer, Jr., Midland, MI (US); Joerg P. Lindner, Himmelpforten (DE)

(73) Assignee: Dow Global Technologies Inc., Midland, MI (US)

( * ) Notice: Subject to any disclaimer, the term of this patent is extended or adjusted under 35 U.S.C. 154(b) by 495 days.

(21) Appl. No.: 10/495,001

(22) PCT Filed: Dec. 4, 2002

(86) PCT No.: PCT/US02/38574

§ 371 (c)(1),
(2), (4) Date: May 10, 2004

(87) PCT Pub. No.: WO03/050100

PCT Pub. Date: Jun. 19, 2003

(65) Prior Publication Data

US 2004/0249176 A1    Dec. 9, 2004

Related U.S. Application Data

(60) Provisional application No. 60/337,954, filed on Dec. 5, 2001.

(51) Int. Cl.
*C07D 301/14* (2006.01)
*C07D 301/03* (2006.01)
*C07D 301/19* (2006.01)

(52) U.S. Cl. .................... 549/525; 549/523; 549/524; 549/529

(58) Field of Classification Search ............... None
See application file for complete search history.

(56) References Cited

U.S. PATENT DOCUMENTS 3,350,422 A    10/1967    Kollar (Continued)

FOREIGN PATENT DOCUMENTS

EP    0 188 912 A2    7/1986

(Continued)

OTHER PUBLICATIONS

Derwent Abstract, AN 1999-432196, "Liquid-Phase Production of Epoxide" (EP 1 266 893 A1).

(Continued)

*Primary Examiner*—Johann Richter
*Assistant Examiner*—Yevgeny Valenrod
(74) *Attorney, Agent, or Firm*—Marie F. Zuckerman (57) ABSTRACT

A process of preparing an olefin oxide, preferably propylene oxide, and an alcohol, such as α-ethylphenyl alcohol, the process involving contacting an olefin, such as propylene, and an organic hydroperoxide, such as ethylbenzene hydroperoxide, in the presence of an epoxidation catalyst, preferably, a homogeneous molybdenum catalyst, in a single reactor system or in a multi-reactor system containing a plurality of sequentially interconnected reactors. Each reactor in the single or multi-reactor system is preferably divided into a plurality of reaction zones designed to facilitate plug flow behavior. The olefin is fed to a first reaction zone in the single reactor system or to a first reactor in the multi-reactor system. The organic hydroperoxide feed is split into a plurality of split organic hydroperoxide feedstreams, and the split feedstreams are distributed throughout the reaction zones, or the reactors, or both.

29 Claims, 2 Drawing Sheets

U.S. PATENT DOCUMENTS

| | | | |
|---|---|---|---|
| 3,351,635 A | 11/1967 | Kollar | |
| 3,360,531 A | 12/1967 | French | |
| 4,217,287 A | 8/1980 | Wu et al. | |
| 4,262,143 A | 4/1981 | Becker | |
| 4,845,251 A | 7/1989 | Marquis et al. | |
| 4,891,437 A | 1/1990 | Marquis et al. | |
| 5,081,267 A | 1/1992 | Rameswaran et al. | |
| 5,093,506 A | 3/1992 | Marquis et al. | |
| 5,107,067 A | 4/1992 | Marquis et al. | |
| 5,274,138 A | 12/1993 | Keating et al. | |
| 5,349,072 A | 9/1994 | Preston et al. | |
| 5,410,077 A | 4/1995 | Wu et al. | |
| 5,573,736 A | 11/1996 | Jubin, Jr. | |
| 5,723,637 A | 3/1998 | Tsuji et al. | |
| 5,760,253 A | 6/1998 | Danner et al. | |
| 5,780,654 A * | 7/1998 | Nemeth et al. | 549/531 |
| 5,840,933 A | 11/1998 | Jubin, Jr. et al. | |
| 5,849,937 A | 12/1998 | Jubin, Jr. et al. | |
| 5,912,367 A | 6/1999 | Chang | |
| 5,977,009 A | 11/1999 | Faraj | |
| 6,096,910 A | 8/2000 | Yamamoto et al. | |
| 6,479,680 B1 | 11/2002 | Bassler et al. | |
| 6,676,906 B1 | 1/2004 | Heisel | |
| 2003/0097009 A1 | 5/2003 | Oku et al. | |
| 2003/0187285 A1 | 10/2003 | Balthsart | |

FOREIGN PATENT DOCUMENTS

| | | |
|---|---|---|
| EP | 0936219 | 8/1999 |
| EP | 1 266 892 A1 | 12/2002 |
| EP | 1 266 893 A1 | 12/2002 |
| GB | 1 218 560 | 1/1971 |
| RU | 1 638 995 | 2/1995 |
| WO | WO 99/32469 | 7/1999 |
| WO | WO 03/074505 A1 | 9/2003 |

OTHER PUBLICATIONS

Derwent Abstract, AN 1995-273775, "Improved Preparation of Popylene Oxide in a Three Reactor Cascade system—by the Reaction of Propylene with Ethyl Benzene Hydro Peroxide in the Presence of a Molybdenum Containing Catalyst" (RU 1 638 995).

Chem Systems International Ltd., PERP Report: Propylene Oxide, Nov. 1990, pp. 40-44. (No cover sheet available).

Chem Systems International Ltd., "Chemical Process Economics," Part I, Propylene Oxide, Dec. 1982, pp. 328-330, 334.

Chem Systems Inc., Report: Propylene Oxide, Apr. 1994, pp. 40-48. Online: www.chemsystems.com; May 11, 2006, pp. 1 and 20, referring to ChemSystems PERP Report, PERP-97/98-7 (Dec. 1998).

* cited by examiner

PROCESS OF PREPARING AN OLEFIN OXIDE FROM OLEFIN AND ORGANIC HYDROPEROXIDE

CROSS-REFERENCE TO RELATED APPLICATIONS

This application is a 371 of International Patent Application No. PCT/US 02/38574, filed Dec. 4, 2002, which claims the benefit of U.S. Provisional Patent Application Ser. No. 60/337,954, filed Dec. 5, 2001.

This invention pertains to an improved process of preparing an olefin oxide, such as propylene oxide, from an olefin, such as propylene, and an organic hydroperoxide, such as, ethylbenzene hydroperoxide. An alcohol, such as α-phenylethyl alcohol, is obtained as a co-product of the process of this invention.

Olefin oxides, preferably propylene oxide, are valuable commodity chemicals that are used to alkoxylate alcohols to form polyalkylene polyether polyols, such as polypropylene polyether polyols, which find significant utility in the manufacture of polyurethanes and synthetic elastomers. More specifically, propylene oxide is also used in the manufacture of propylene glycol and dipropylene glycol as well as isopropanolamine. Propylene glycol finds utility as an antifreeze and brake fluid and in the manufacture of polyurethanes and polyester resins. Dipropylene glycol also finds utility in the manufacture of resins. Isopropanolamine finds utility in surfactant formulations.

Processes are known for preparing olefin oxides, such as propylene oxide, by the liquid phase reaction of an olefin, such as propylene, with certain organic hydroperoxides, such as, tertiary butyl hydroperoxide, cumene hydroperoxide, or ethylbenzene hydroperoxide, as disclosed, for example, in U.S. Pat. No. 3,350,422 and U.S. Pat. No. 3,351,635. The processes are taught to be conducted in batch reactors that offer acceptable control of reaction temperature, but lack acceptable productivity for commercialization. More particularly, U.S. Pat. No. 3,350,422 teaches the use of vanadium naphthenate as a catalyst and staged addition of the organic hydroperoxide to the batch reactor. Disadvantageously, the selectivity to olefin oxide, particularly propylene oxide, achieved by the disclosed process is low.

U.S. Pat. No. 3,351,635 discloses a similar process that is conducted in the presence of a catalytic amount of a molybdenum, tungsten, titanium, columbium, tantalum, rhenium, selenium, chromium, zirconium, tellurium, or uranium catalyst. Incremental and staged additions of the organic hydroperoxide to the reaction are disclosed. When ethylbenzene hydroperoxide is used as the oxidant, the disclosed process achieves an unacceptable hydroperoxide conversion and an unacceptable selectivity to propylene oxide, based on hydroperoxide converted. Specifically, an ethylbenzene hydroperoxide conversion of only 79 percent and a selectivity to propylene oxide of only 72 percent are obtained.

Various other engineering realizations of the reaction of an olefin with an organic hydroperoxide have been evaluated and disclosed. In U.S. Pat. No. 5,840,933 a solid catalyst is employed in a series of separate reaction zones. The olefin, for example, propylene, and hydroperoxide oxidant, for example, ethylbenzene hydroperoxide, are combined into one feed, and the combined feed is fed to each reaction zone. The main attractiveness of the design appears to be management of the heat produced by the exothermic reaction; but the process offers no particular enhancement in selectivity to olefin oxide.

In U.S. Pat. No. 5,849,937 another process is disclosed for the reaction of an olefin, such as propylene, and an organic hydroperoxide, such as ethylbenzene hydroperoxide, in a multiple reactor system using a heterogeneous catalyst. The design provides for removing from service one or more reactors in a series of interconnected reactors to enable regeneration of the deactivated catalyst. Again, the olefin feed is combined with the hydroperoxide feed, and the combined feed is fed to the selected reactors. The process offers no particular enhancement of selectivity to olefin oxide, more specifically, propylene oxide.

Additionally, U.S. Pat. No. 5,410,077 discloses the reaction of propylene with tertiary butyl hydroperoxide in the presence of t-butyl alcohol and a homogeneous molybdenum catalyst in a reactor system comprising a first isothermal segment and a second adiabatic segment. The adiabatic segment is added to obtain additional conversion of the hydroperoxide. The isothermal segment is further taught to comprise a plurality of at least four sequentially interconnected internally cooled reactors. In this reactor system, the total tertiary butyl hydroperoxide feed is split, so as to provide a portion of the total tertiary butyl hydroperoxide feed to each of the reactors in the isothermal segment. By limiting the quantity of tertiary butyl hydroperoxide fed to each reactor in the isothermal segment, the reaction exotherm is controlled and the reaction temperature remains essentially isothermal. As with other prior art, U.S. Pat. No. 5,410,077 appears to be silent with respect to plug flow behavior. Additionally, U.S. Pat. No. 5,410,077 is silent with respect to the feasibility of replacing tertiary butyl hydroperoxide with ethylbenzene hydroperoxide.

It is known that ethylbenzene hydroperoxide facilitates the epoxidation of olefins, such as propylene, at a faster rate than tertiary butyl hydroperoxide; however, the use of ethylbenzene hydroperoxide poses special problems. Ethylbenzene hydroperoxide is significantly less stable than tertiary butyl hydroperoxide. Moreover, whereas tertiary butyl hydroperoxide decomposes by essentially one pathway to form tertiary butyl alcohol, ethylbenzene hydroperoxide decomposes by a variety of pathways to form a variety of decomposition products, including α-phenylethyl alcohol (α-methylphenyl carbinol), acetophenone, and benzoic acid, among others. Accordingly, the selectivity to olefin oxide, based on the moles of organic hydroperoxide converted, is typically lower when ethylbenzene hydroperoxide is employed as the oxidant, as compared with tertiary butyl hydroperoxide.

In view of all of the above, it would be desirable to discover an improved process of preparing an olefin oxide, such as propylene oxide, preferably using ethylbenzene hydroperoxide as the oxidant in place of tertiary butyl hydroperoxide. Such a process would benefit from the increased epoxidation rate provided by ethylbenzene hydroperoxide. Such a process could therefore be beneficially operated at a lower temperature than the analogous process with tertiary butyl hydroperoxide while still achieving a comparable hydroperoxide conversion. More preferably, it would be desirable to achieve the higher epoxidation rate and comparable organic hydroperoxide conversion at an improved selectivity to olefin oxide, based on moles of organic hydroperoxide converted. Acceptable control of the reaction exotherm is also a desired outcome, as well as safe handling of the organic hydroperoxide. A process with all of the aforementioned properties would provide an attractive and more productive method of preparing olefin oxide, as compared with prior art methods.

This invention provides for a novel and improved process of preparing an olefin oxide and a co-product alcohol. The invention generally comprises contacting a liquid phase comprising an olefin and an organic hydroperoxide in the presence of an epoxidation catalyst under process conditions sufficient to prepare the olefin oxide and the co-product alcohol. In the particular features of this invention, the contacting of the olefin and the organic hydroperoxide is conducted in a reactor system that provides for the staged addition of the organic hydroperoxide, characterized in that a primary organic hydroperoxide feed is split into a plurality of organic hydroperoxide feedstreams (hereinafter referred to as "split organic hydroperoxide feedstreams"), and the split organic hydroperoxide feedstreams are distributed among reaction zones, or reactors, or both, in the reaction system. As a further feature of the novel process of this invention, the reactor system is designed to facilitate plug flow behavior of the liquid phase.

Under the novel process conditions of this invention, an olefin oxide and a co-product alcohol are prepared from an olefin and an organic hydroperoxide. In a preferred embodiment of the invention, propylene and ethylbenzene hydroperoxide are used to prepare propylene oxide and the corresponding co-product of α-phenylethyl alcohol. By using ethylbenzene hydroperoxide as the oxidant, an improved reaction rate is achieved, as compared with using tertiary butyl hydroperoxide as the oxidant. If desired, the preferred process of this invention may be run at a lower temperature than the analogous process with tertiary butyl hydroperoxide, while still achieving a comparable hydroperoxide conversion. As a further general advantage of this invention, the staged addition of the organic hydroperoxide beneficially provides acceptable control over process temperature and improved safety of handling the hydroperoxide. In a preferred embodiment of the invention, a cooling means is associated with each reactor, thereby allowing the process to proceed advantageously at a controlled optimal temperature. As yet another advantage of this invention, the reactor system can be easily maintained at the essentially autogenous pressure required to keep the reactants in the liquid phase. Most advantageously, in the process of this invention, the reactor design minimizes back-mixing, that is, the flow of elements of the reaction fluid in directions other than the forward direction of the bulk reaction mixture. Back-mixing occurs when not all liquid phase elements have the same residence time in the reactor, and back-mixing has been found to be detrimental to the yield of olefin oxide obtained. Thus, the minimization or elimination of back-mixing is desirable. As compared with prior art processes, the novel combination of operating features described hereinabove provides for an improved process of producing olefin oxide, preferably propylene oxide, at significantly higher selectivity, based on hydroperoxide oxidant converted.

The novel invention set forth herein pertains to a process of preparing an olefin oxide and a co-product alcohol. The invention in its broadest concept comprises contacting a liquid phase comprising an olefin and an organic hydroperoxide in the presence of an epoxidation catalyst under process conditions sufficient to prepare the olefin oxide and the co-product alcohol. In this invention, the contacting of the olefin and the organic hydroperoxide is conducted in a reactor system that provides for the staged addition of the organic hydroperoxide, characterized in that a primary organic hydroperoxide feed is split into a plurality of organic hydroperoxide feedstreams (hereinafter referred to as "split organic hydroperoxide feedstreams"), and the split organic hydroperoxide feedstreams are distributed among reaction zones, or reactors, or both, in the reaction system. As a further novel feature of the process of this invention, the reactor system is designed to facilitate plug flow behavior of the liquid phase.

In a preferred embodiment, the novel process of this invention relates to the preparation of propylene oxide and a co-product alcohol. The invention in this preferred embodiment comprises contacting a liquid phase comprising propylene and an organic hydroperoxide in the presence of an epoxidation catalyst under process conditions sufficient to prepare propylene oxide and co-product alcohol. The novel process comprises a combination of features that provide for increased selectivity to propylene oxide, based on organic hydroperoxide oxidant reacted. In particular, the process comprises contacting propylene and organic hydroperoxide in a reactor system designed for the staged addition of the organic hydroperoxide, characterized in that a primary organic hydroperoxide feed is split into a plurality split organic hydroperoxide feedstreams, and the split organic hydroperoxide feedstreams are distributed among the reaction zones, or reactors, or both, in the reactor system. As a further feature of the novel process of this invention, the reactor system is designed to facilitate plug flow behavior, so as to reduce back-mixing of the liquid phase. Back-mixing occurs when elements of the liquid phase reaction mixture flow in directions other than the forward direction of the bulk reaction mixture, and in consequence, not all fluid elements experience the same history as they pass through the reactor. Back-mixing has been found to be detrimental to the yield of olefin oxide obtained. Thus, the minimization or elimination of back-mixing is desirable.

In a more preferred embodiment, the invention comprises contacting a liquid phase comprising propylene and ethylbenzene hydroperoxide in the presence of an epoxidation catalyst under process conditions sufficient to prepare propylene oxide and α-phenylethyl alcohol. The novel process of this invention further comprises a combination of features that provide for increased selectivity to propylene oxide based on ethylbenzene hydroperoxide oxidant reacted. In particular, the process comprises contacting propylene and ethylbenzene hydroperoxide in a reactor system designed for the staged addition of the ethylbenzene hydroperoxide, characterized in that a primary ethylbenzene hydroperoxide feed is split into a plurality of ethylbenzene hydroperoxide feedstreams, and the split ethylbenzene hydroperoxide feedstreams are distributed among the reaction zones, or reactors, or both, in the reactor system. As a further feature of the preferred process, the reactor system comprises one or more means for facilitating plug flow behavior.

In another preferred embodiment, the reactor system employed in the aforementioned process of this invention comprises a single reactor that is divided into a plurality of sequentially interconnected reaction zones. The reactor further comprises one or more means to facilitate plug flow behavior of the liquid phase, and the reactor is also associated with a cooling means. By means of operation, the olefin is fed to a first reaction zone in the single reactor system. In contrast, the total organic hydroperoxide feed is added to the reactor system in stages by splitting the feed into a plurality of split organic hydroperoxide feedstreams and distributing the split organic hydroperoxide feedstreams to the plurality of reaction zones in the reactor system. In a more preferred mode of operation, a split organic hydroperoxide feed is fed to each reaction zone. In another more preferred mode, a portion of the organic hydroperoxide and optionally catalyst is fed to the first reaction zone, while the balance of the organic hydroperoxide and optionally catalyst is fed to a zone located at the mid-point of the reactor (plus or minus one reactor zone). The portions may be divided equally or by any other fraction as desired.

In another preferred embodiment, the reactor system employed in the aforementioned process of this invention is a multi-reactor system comprising a plurality of sequentially interconnected reactors. Each reactor in this multi-reactor system is divided into a plurality of sequentially interconnected reaction zones. Moreover, each reactor is designed with one or more means to facilitate plug flow behavior. In this preferred embodiment, each reactor in the reactor system is also associated with a cooling means. By way of operation, the olefin is fed to a first reactor in the multi-reactor system. In contrast, the total organic hydroperoxide feed is added to the reactor system in stages by splitting the feed into a plurality of split organic hydroperoxide feedstreams and distributing the split organic hydroperoxide feedstreams to the reactor system. More specifically, the plurality of split organic hydroperoxide feedstreams is distributed among the plurality of sequentially interconnected reactors in the multi-reactor system. In a more preferred mode of operation, each reactor is fed with one of the split hydroperoxide feedstreams. In another preferred mode, a portion of the organic hydroperoxide and optionally catalyst is fed to the first reactor, while the balance of the hydroperoxide and optionally catalyst is fed to a reactor located at the mid-point of the multi-reactor system (plus or minus one reactor). The portions may be divided equally or by any other fraction as desired.

In a most preferred embodiment of the single reactor system, the reactor is divided into 4 or more reaction zones, which are sequentially interconnected and designed to facilitate plug flow behavior. In a most preferred embodiment of the multi-reactor system, the plurality of sequentially interconnected reactors comprises 2 or more reactors; each designed to facilitate plug flow behavior, more preferably, by each being segmented into 4 or more reaction zones. In another more preferred embodiment of this invention, each reactor in the plurality of sequentially interconnected reactors is an adiabatic reactor.

While the process of this invention may be employed with any organic hydroperoxide, at this time the preferred organic hydroperoxide is selected from ethylbenzene hydroperoxide and cumene hydroperoxide, or a mixture thereof.

A detailed description of FIGS. 1 and 2 follows hereinafter. Where the description refers to the use of ethylbenzene hydroperoxide, it should be understood that any other operable organic hydroperoxide may be substituted for ethylbenzene hydroperoxide, including cumene hydroperoxide. Likewise, where the description refers to propylene, it should be understood that any other operable olefin may be substituted for propylene. Accordingly, the composition of the product stream will depend upon the specific olefin and organic hydroperoxide employed.

Figure 1:
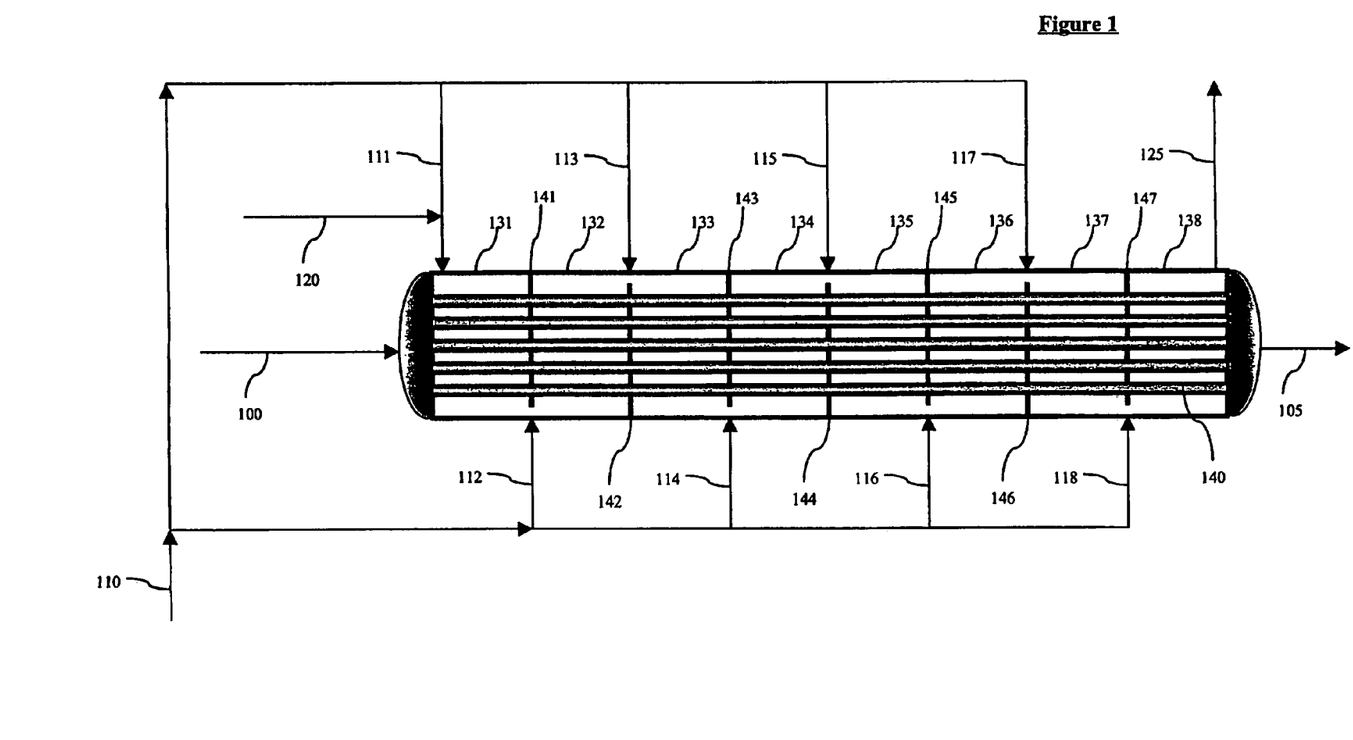
FIG. 1 illustrates a preferred embodiment of the process of this invention, wherein the process is conducted in a reactor system comprising a single reactor divided into a plurality of sequentially interconnected reaction zones designed to facilitate plug flow behavior. Olefin, preferably propylene, is fed to a first reaction zone, whereas the organic hydroperoxide, preferably ethylbenzene hydroperoxide, is fed to each reaction zone.

With reference to FIG. 1, a preferred reactor system is illustrated comprising a single horizontally-oriented, isothermal reactor that is divided into eight reaction zones (131, 132, 133, 134, 135, 136, 137, and 138). The reaction zones are formed by seven partitions inside the reactor (141, 142, 143, 144, 145, 146, 147), each partition being essentially perpendicular relative to the horizontal axis of the reactor, and preferably, each partition consisting of a baffle attached at one end to the inside wall of the reactor. In the illustration shown, the baffle does not reach entirely to the opposing interior wall, but rather stops short of the opposing interior wall, thereby leaving an open space between the edge of the baffle and the wall. The open space is designed to provide for fluid flow from one reaction zone to the next; but the space is preferably not so large as to allow substantial fluid back-mixing. The presence of 3 or more baffles and 4 or more reaction zones typically provides for essentially plug flow behavior in the reactor. While some back-mixing may occur within a given reaction zone, essentially no backmixing occurs between successive reaction zones. While the number of baffles and reaction zones will depend upon the scale and design of the reactor, generally, each reactor comprises less than 15 reaction zones, preferably, less than 12 reaction zones. In the preferred embodiment illustrated in FIG. 1, the reactor is equipped with internal cooling coils (shaded horizontal lines, illustrated by 140) that are capable of maintaining isothermality of the liquid phase. A heat transfer fluid or liquid refrigerant enters the cooling coils via heat transfer fluid feed line 100. Heat transfer fluid or liquid refrigerant exits the cooling coils via heat transfer fluid exit line 105. A solution containing the propylene feed, catalyst, and solvent enters the reactor through feed line 120. A primary ethylbenzene hydroperoxide feed, shown as ethylbenzene hydroperoxide feed line 110, is split into eight split ethylbenzene hydroperoxide feed lines (111, 112, 113, 114, 115, 116, 117, and 118), each of which is distributed to one of the reaction zones or fed at the intersection of two adjoining reaction zones. Optionally, the catalyst feed may also be split and fed with the ethylbenzene hydroperoxide. In FIG. 1 the heat transfer fluid and the reactant feedstream are shown to be flowing in the same direction; however, an alternative embodiment is acceptable wherein the heat transfer fluid flows in a countercurrent direction versus the flow of the reactant feedstream. A product stream comprising propylene oxide, α-phenylethyl alcohol, solvent, catalyst, unreacted propylene, and unreacted ethylbenzene hydroperoxide, if any, and by-products, typically acetophenone, exits the reactor through product line 125. The effluent product stream in effluent product line 125 is transmitted to a separations unit (not shown in figure) for recovery of products, namely, propylene oxide and α-phenylethyl alcohol. Unreacted raw materials, such as propylene, as well as solvent and catalyst, may be recovered from effluent line 125 and recycled to the reactor. In an alternative embodiment, the reactor of FIG. 1 is reiterated in a plurality of reactors connected in series.

Figure 2:
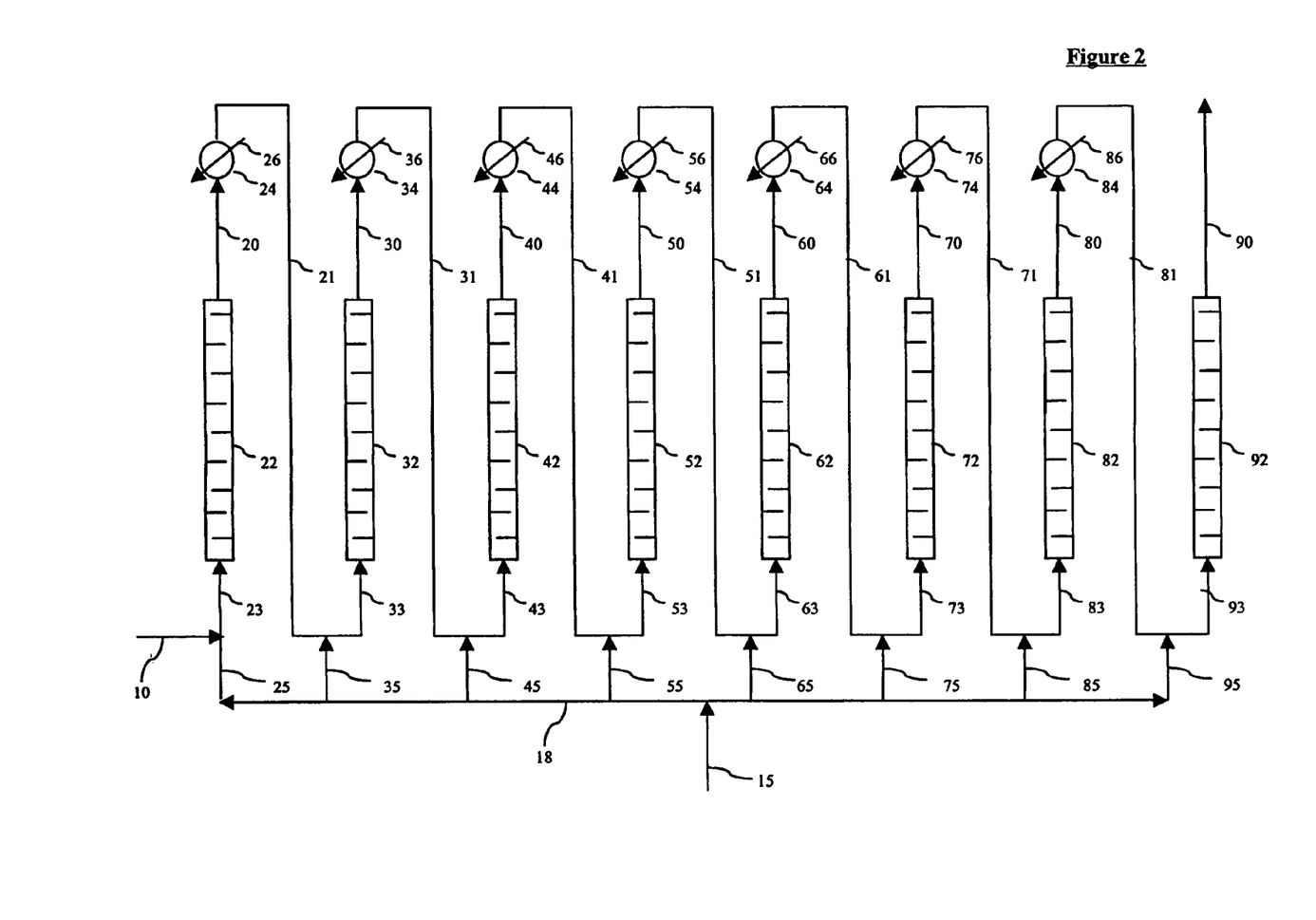
FIG. 2 illustrates a second preferred embodiment of the process of this invention, wherein the process is conducted in a multi-reactor system comprising a plurality of sequentially interconnected reactors. Each reactor is divided into a plurality of sequentially interconnected reaction zones designed to facilitate plug flow behavior. Olefin, preferably propylene, is fed to the first reactor in the reactor system, whereas the organic hydroperoxide, preferably ethylbenzene hydroperoxide, is fed to each reactor in the multi-reactor system.

With reference to FIG. 2, a preferred multi-reactor system is illustrated comprising eight sequentially interconnected, vertically-oriented reactors (units 22, 32, 42, 52, 62, 72, 82, and 92). Each reactor is individually either an isothermal or adiabatic reactor, preferably, an adiabatic reactor. Internally, each reactor is divided into a plurality of sequentially interconnected reaction zones in the manner described in FIG. 1. In FIG. 2, heat control is external to the reactors, such that a heat exchanger is situated between each adjoining pair of reactors (units 24, 34, 44, 54, 64, 74, and 84). Primary feeds are provided as feed lines 10, 15, and 18. Primary feed line 10 is a supply line for an initial feed comprising propylene, solvent (for example, ethylbenzene or cumene), and epoxidation catalyst. Primary feed line 15, which continues as feed line 18, provides a supply line comprising ethylbenzene hydroperoxide and solvent. In FIG. 2, primary ethylbenzene hydroperoxide feed in feed line 18 is split into eight ethylbenzene hydroperoxide split feeds as split hydroperoxide feed lines (25, 35, 45, 55, 65, 75, 85, and 95). Optionally, epoxidation catalyst, if desired, may be added to any one of the split hydroperoxide feed lines at a point close to the reactor inlet. In the process, an initial feed comprising propylene, solvent, and epoxidation catalyst in primary feed line 10 is combined with ethylbenzene hydroperoxide split feed from ethylbenzene hydroperoxide split feed line 25 to form a combined reagent feed in feed line 23, comprising propylene, ethylbenzene hydroperoxide, solvent, and epoxidation catalyst, which is fed to the first reactor unit 22. (Beneficially, the combined feeds should be adequately mixed prior to introduction to the reactor.) A first product effluent stream comprising propylene oxide, α-phenylethyl alcohol, solvent, unreacted propylene, catalyst, unreacted ethylbenzene hydroperoxide if any, and any by-products, such as acetophenone, is obtained from first reactor 22 as first product effluent stream 20. First product effluent stream 20 is passed through heat exchanger 24 wherein the effluent stream is cooled with cooling liquid in cooling liquid line 26 (arrow 26), to recover a heat-exchanged first product effluent stream in heat exchanged first product effluent stream line 21. The heat exchanged first product effluent stream in heat exchanged first product effluent stream line 21 is combined with a second split ethylbenzene hydroperoxide feed obtained from split hydroperoxide feed line 35 to form a second combined reactant feed stream in combined reactant feed line 33, comprising propylene oxide, α-phenylethyl alcohol, solvent, unreacted propylene, ethylbenzene hydroperoxide, and catalyst. The second combined reactant feed of second combined reactant feed line 33 is fed to the second reactor 32 from which a second effluent product stream comprising solvent, propylene oxide, α-phenylethyl alcohol, unreacted propylene, catalyst, and unreacted ethylbenzene hydroperoxide if any, is obtained as second effluent product line 30. Second effluent product stream in second effluent product line 30 is then passed through a second heat exchanger 34, with cooling lines 36 for cooling liquid, to yield a second heat-exchanged effluent stream in second heat exchanged effluent line 31. Thereafter, second heat exchanged effluent in second heat exchanged effluent line 31 is combined with third split ethylbenzene hydroperoxide feed obtained from third split ethylbenzene hydroperoxide feed line 45 to form a third combined reactant feed comprising propylene oxide, α-phenylethyl alcohol, solvent, unreacted propylene, ethylbenzene hydroperoxide, and catalyst as third combined reactant feed line 43. Third combined reactant feed from third combined reactant feed line 43 is fed to third reactor unit 42, from which a third reactor effluent steam, also comprising solvent, propylene oxide, α-phenylethyl alcohol, unreacted propylene, catalyst, and unreacted ethylbenzene hydroperoxide if any, is obtained as third effluent product line 40. Third effluent product stream in third effluent product line 40 is then passed through a third heat exchanger 44, also equipped with cooling lines 46 for cooling liquid, to yield a third heat-exchanged effluent product steam as third heat exchanged effluent product line 41, which is combined with a fourth split ethylbenzene hydroperoxide feed from fourth split ethylbenzene hydroperoxide feed line 55 to form a fourth reactant feed in fourth reactant feed line 53. Fourth reactant feed comprising propylene oxide, α-phenylethyl alcohol, unreacted propylene, ethylbenzene hydroperoxide, and catalyst in fourth reactant feed line 53 is fed to fourth reactor 52, from which a fourth reactor effluent stream comprising solvent, propylene oxide, α-phenylethyl alcohol, unreacted propylene, catalyst, and unreacted ethylbenzene hydroperoxide if any, is obtained as fourth effluent product line 50. Fourth effluent product stream in fourth effluent product line 50 is then passed through a fourth heat exchanger 54, equipped with cooling liquid in cooling line 56, to yield a fourth heat-exchanged effluent product stream in fourth heat exchanged effluent product line 51. Thereafter, fourth heat exchanged effluent product stream in fourth heat exchanged effluent product line 51 is combined with a fifth split ethylbenzene hydroperoxide feed from fifth split ethylbenzene hydroperoxide feed line 65 and the process is reiterated. In the reiteration sequence, reactors 62, 72, 82, and 92 are employed with reactant feed streams 63, 73, 83 and 93 respectively. Each reactant feed stream comprises a fresh portion of ethylbenzene hydroperoxide obtained from fifth, sixth, seventh, and eighth split ethylbenzene hydroperoxide feeds obtained from split ethylbenzene hydroperoxide feed lines 65, 75, 85, and 95, respectively. The reactant stream further comprises an effluent product stream of propylene oxide, α-phenylethyl alcohol, unreacted propylene, catalyst, and unreacted ethylbenzene hydroperoxide if any, obtained respectively from heat exchanged effluent product lines 51, 61, 71, and 81. Each of the respective effluent product streams from reactors 62, 72, and 82 is obtained as an a effluent product line 60, 70, and 80, respectively; and each product effluent is passed through heat exchangers 64, 74, or 84, respectively, to yield heat exchanged effluent product streams from effluent product lines 61, 71, and 81. The final effluent product stream in effluent product line 90, obtained from reactor 92, is transmitted to a plurality of separations units (not shown in figure) for recovery of products, particularly, propylene oxide and α-phenylethyl alcohol. Unreacted raw materials, such as propylene, as well as ethylbenzene and catalyst can also be recovered from effluent line 90 and recycled to any reactor in the reactor system, preferably, the first reactor.

The olefin employed in the process of this invention may include any olefinically unsaturated compound that is capable of being epoxidized by organic hydroperoxide to the corresponding olefin oxide (oxirane). Such compounds may suitably include substituted and unsubstituted aliphatic and alicyclic olefins, including olefinic hydrocarbons, and olefinically unsaturated esters, alcohols, ketones, and ethers. Preferred olefins are those having from 2 to 30 carbon atoms, and preferably, at least 3 carbon atoms. Illustrative olefins include, without limitation, propylene, n-butylene, isobutylene, the pentenes, the methyl pentenes, hexenes, heptenes, octenes, dodecenes, cyclohexene, methylcyclohexene, butadiene, styrene, methylstyrene, vinyl toluene, and vinylcyclohexene. Substituted olefins suitable for the process include, without limitation, allyl alcohol, methallyl alcohol, cyclohexanol, diallyl ether, methyl methacrylate, methyl oleate, methyl vinyl ketone, and allyl chloride. Preferably, the olefin is a $C_{3-8}$ olefin, more preferably, propylene.

The organic hydroperoxide employed in the process of this invention may include any organic compound with at least one hydroperoxy functional group (—OOH) that is capable of transferring one of the oxygen atoms to an olefin to form an olefin oxide. Exemplary organic hydroperoxides include, without limitation, ethylbenzene hydroperoxide, cumene hydroperoxide, cyclohexyl hydroperoxide, and t-butyl hydroperoxide. Methods are known in the art for preparing organic hydroperoxides; for example, the preparation of ethylbenzene hydroperoxide from ethylbenzene and oxygen, is found, for example, in U.S. Pat. No. 4,066,706 and U.S. Pat. No. 4,262,143, incorporated herein by reference. In the process of this invention, the organic hydroperoxide is typically supplied in a liquid phase with a suitable solvent. Any solvent may be employed that is thermally stable and essentially non-reactive under the prevailing process conditions. Suitable solvents include aromatics, such as benzene, xylenes, ethylbenzene, cumene, and naphthalenes. Preferably, the solvent is ethylbenzene or cumene. To enhance the epoxidation kinetics, the organic hydroperoxide is often concentrated. Generally, the organic hydroperoxide is provided in the solution in a concentration greater than 5 weight percent, and preferably, greater than 20 weight percent. Generally, the organic hydroperoxide is provided in the solution in a concentration less than 40 weight percent, and preferably, less than 35 weight percent.

Generally, the olefin is provided to the reactor as a liquid; for example, propylene as a compressed liquid. Any diluent may be employed with the olefin, provided that the diluent is essentially inert with respect to the process and catalyst. Suitable diluents include alkanes and alkylaromatics, and other organic solvents not found to affect the reaction kinetics or yield. If a diluent is used, then the concentration of olefin in the diluent may be any concentration, provided that the process produces olefin oxide. Typically, the olefin concentration will be greater than 5 mole percent, preferably, greater than 20 mole percent, based on the total moles of olefin and diluent. Typically, the olefin concentration will be less than 100 mole percent, based on the total moles of olefin and diluent.

In the process of this invention the ratio of moles of olefin to total moles of organic hydroperoxide fed to the process may vary widely, provided that olefin oxide is produced as a product. The term "total moles of organic hydroperoxide" refers to the sum of the moles of organic hydroperoxide fed to the reactor system. Generally, the molar ratio of olefin to total organic hydroperoxide is greater than 2:1, preferably, greater than 4:1. Generally, the molar ratio of olefin to total organic hydroperoxide is less than 15:1, preferably, less than 10:1. Although the molar ratio of olefin to total organic hydroperoxide may range from greater than 2:1 to less than 15:1, the molar ratio of olefin to organic hydroperoxide in each reaction zone or each reactor in the reactor system may be considerably higher than 15:1. As an example, if the molar ratio of propylene to total ethylbenzene hydroperoxide is 5:1, and five reactors are connected in series with the ethylbenzene hydroperoxide feed being equally divided among the five reactors, then the propylene to ethylbenzene hydroperoxide molar ratio in each reactor will be 25:1. In this manner, organic hydroperoxide is provided to each reaction zone or each reactor, as the case may be, in a relatively low concentration, which prevents the hydroperoxide from prematurely decomposing and facilitates control over the reaction exotherm.

Any epoxidation catalyst may be employed in the process of this invention, provided that the catalyst is capable of transferring oxygen from the organic hydroperoxide to an olefin so as to form olefin oxide. Many such catalysts are known to those skilled in the art including, for example, molybdenum-containing catalysts and titanium-containing catalysts, as disclosed, for example, in U.S. Pat. No. 3,350,422, U.S. Pat. No. 3,351,635, U.S. Pat. No. 4,217,287, U.S. Pat. No. 4,262,143, U.S. Pat. No. 4,845,251, U.S. Pat. No. 5,081,267, U.S. Pat. No. 5,107,067, U.S. Pat. No. 5,723,637, U.S. Pat. No. 5,912,367, and U.S. Pat. No. 6,096,910, the aforementioned patents being incorporated herein by reference. Suitable molybdenum-containing catalysts include, without limitation, molybdenum organic salts, such as molybdenum naphthenate, acetate, stearate, butyrate, 2-ethyl hexanoate, and iso-octanoate; molybdenum inorganic salts and oxides, such as ammonium molybdate, ammonium dimolybdate, ammonium heptamolybdate, molybdenum trioxide; molybdenum chlorides, and molybdenum oxychlorides as well as any hydrated forms of the aforementioned oxides and salts. Optionally, any of the aforementioned molybdenum-containing catalysts may also contain one or more alkali metal oxides and/or hydroxides. Organomolybdenum complexes, preferably, complexes of molybdenum with alkylene glycols, may also be suitably employed as the catalyst, optionally combined with one or more alkali metal oxides and/or hydroxides. Suitable titanium-containing catalysts include, without limitation, titanium-containing silicon oxides, titanosilicates, such as titanium silicalite, and various supported realizations thereof. Combinations of molybdenum oxide and titanium oxide dispersed on silica may also be suitably employed. More preferably, the catalyst is molybdenum naphthenate, molybdenum 2-ethyl hexanoate, or molybdenum iso-octanoate.

The catalyst can be provided in homogeneous form, that is, dissolved in the liquid phase reaction mixture comprising solvent and dissolved olefin. Typically, a solution containing olefin, solvent, and the homogeneous catalyst is provided to the first reaction zone in the single reactor system or to the first reactor in the multi-reactor system. Optionally, a solution containing catalyst can be supplied to each reaction zone in the single reactor system or to each reactor in the multi-reactor system; or supplied to more than one, but not necessarily all of the reaction zones or reactors in the sequence, if additional catalyst is desired. In a preferred embodiment, for example, a portion of the catalyst may be added to the first reaction zone, and the balance of catalyst may be added to a reaction zone at the mid-point of the reactor (plus or minus one reaction zone). Alternatively, a portion of the catalyst may be added to the first reactor, and the balance of the catalyst may be added at the mid-point of the multi-reactor train (plus or minus one reactor). The portions of catalyst may be divided equally or by any other fraction, as desired. As another alternative, the catalyst can be provided as a heterogeneous catalyst, that is, in a solid phase separate from the liquid phase reaction medium. If the catalyst is heterogeneous, then the catalyst can be supported on any conventional catalyst support, including without limitation, silica, alumina, titania, zirconia, and/or aluminosilicates. In heterogeneous form the catalyst is generally provided in a fixed-bed situated within each reaction zone in the reactor system. More preferably, the catalyst is a homogeneous catalyst. Most preferably, the catalyst is a homogeneous molybdenum catalyst selected from molybdenum naphthenate, molybdenum 2-ethyl hexanoate, and molybdenum iso-octanoate.

The quantity of catalyst used in the process will vary depending upon the specific catalyst chosen. If the catalyst is a homogeneous catalyst, then the concentration of catalyst is generally greater than 0.0001, and preferably, greater than 0.0005 mole catalyst per mole organic hydroperoxide. Generally, the concentration of the homogeneous catalyst is less than 0.0100, and preferably less than 0.0080 mole catalyst per mole organic hydroperoxide. If the catalyst is provided as a separate solid phase, then the space velocity of the organic hydroperoxide (OHP) (for example, weight of OHP per weight catalyst per hour) will determine the relative ratio of organic hydroperoxide employed per weight of catalyst, as noted hereinafter.

From the description of the process invention hereinabove, one skilled in the art will appreciate that the total organic hydroperoxide feed is split, and the split hydroperoxide feeds are distributed throughout the reactor system. Preferably, the plurality of split organic hydroperoxide feeds are distributed among (a) the plurality of sequentially interconnected reaction zones in the single reactor system, or (b) the plurality of sequentially interconnected reactors in the multi-reactor system. Likewise, if the catalyst is homogenous, the solution containing the catalyst may be split and provided to one or more reaction zones or reactors in the reactor system. All of the individual feedstreams comprising solvent, olefin, organic hydroperoxide, and catalyst fed to the reaction zones and/or individual reactors may be formulated to be identical to each other, or alternatively, each feedstream may be formulated independently of the other feedstreams. No matter what realization is employed, the reaction temperature can be adequately controlled by manipulation of the reagent and catalyst concentrations and with cooling means; and a high selectivity to propylene oxide can be achieved.

As noted hereinbefore, the reactor system employed in the process of this invention comprises either a single reactor with multiple reaction zones, or a plurality of sequentially interconnected reactors, preferably, each with multiple reaction zones. The single reactor or each reactor in the plurality of sequentially interconnected reactors is typically horizontally or vertically oriented. In one preferred embodiment of the invention, the reactor system comprises a horizontally-oriented reactor, as illustrated in FIG. 1. Such a reactor preferably contains 4 or more reaction zones, but less than 15 reaction zones. More preferably, the reactor contains two feed points for the hydroperoxide feed, and optionally, the catalyst feed. A first feed point is preferably located at or near the front end of the reactor, and a second feed point is preferably located at the midpoint of the reactor (plus or minus one reaction zone). The feed point is usually at the front end inlet of the reaction zone; but could be elsewhere in the reaction zone as designed by one skilled in the art. In another preferred embodiment, the reactor system comprises a plurality of sequentially interconnected, vertically-oriented reactors, as illustrated in FIG. 2, more preferably, with each reactor segmented into a plurality of reaction zones. Typically, the plurality of sequentially interconnected reactors will comprise 2 or more reactors. Typically, the plurality of sequentially interconnected reactors will comprise less than 12 reactors, preferably, less than 10 reactors. A preferred embodiment of 8 sequentially interconnected, vertically-oriented reactors is illustrated in FIG. 2 (units 22, 32, 42, 52, 62, 72, 82, and 92). In another preferred embodiment, the plurality of sequentially interconnected reactors comprises 2 or more reactors, each designed to facilitate plug flow behavior, by more preferably being segmented into 4 or more reaction zones. In a most preferred embodiment thereof, there are two feed points for the hydroperoxide feed, and optionally, the catalyst feed. A first feed point is located at or near the front end of the first reactor; and a second feed point is located at or near the midpoint of the multi-reactor system (plus or minus one reactor). Again, the feed point is usually located at the front end inlet of each reactor; but may be elsewhere on the reactor as designed by one skilled in the art.

In the single reactor system, the single reactor typically comprises an isothermal reactor complete with internal cooling coils for circulation of a heat transfer fluid or refrigerant. In the multi-reactor system, each of the plurality of reactors may be selected from isothermal and adiabatic reactors. Typically, the term "isothermal reactor" implies that a reactor's internal space is maintained at essentially one temperature throughout the process cycle. In the process of this invention, however, the term "isothermal reactor" shall be construed more flexibly to include reactors wherein the temperature is maintained at ±10° C. of a target process temperature. The target process temperature may be any operable temperature selected for the process, as noted hereinafter. The term "adiabatic reactor" shall mean that essentially no heat is removed from the reactor. Accordingly, an external cooling means is typically associated with each adiabatic reactor. Preferably, each of the reactors in the multi-reactor system is an adiabatic reactor.

In addition, the reactor system comprises one or more means to facilitate plug flow behavior, so as to minimize back-mixing of the liquid reaction phase. Back-mixing has been defined hereinbefore as the movement of fluid wherein not all fluid elements have the same history as they pass through the reactor. Back-mixing has been found to be detrimental to the productivity of the process. It is believed that back-mixing increases the residence time of random fluid elements (as compared with the average residence time), thereby reducing selectivity to olefin oxide; and decreases the residence time of other random fluid elements (as compared with the average), thereby reducing peroxide conversion. In contrast, plug flow involves the bulk forward movement of fluid flow from the entrance port to the exit port of the reactor, such that essentially all fluid elements have essentially the same history (residence time) as they pass through the reactor. Whereas laboratory scale reactors may simulate plug flow behavior in the absence of any special design features, commercial scale equipment typically requires internal structures designed to facilitate plug flow behavior. Preferably, each commercial scale reactor in the single or multi-reactor system contains one or more means for facilitating plug flow, preferably, one or more partitions that are attached to an interior wall of the reactor, thereby dividing the space encompassed by the reactor into distinct reaction zones. More preferably, each partition comprises a baffle attached to an inner wall of the reactor. The partition, preferably baffle, is typically oriented essentially perpendicular to the longitudinal axis of the reactor, and extends across the reactor, but, for example in one design, not entirely to the opposing wall. Between the opposing wall and the partition, an open access is provided to allow for fluid flow from one zone to the next. The open access is large enough to facilitate flow of the liquid reaction phase from one zone to the next, but not so large as to produce unacceptable back-mixing. These baffles may provide flow from chamber to chamber by sieves properly sized to prevent backmixing, or by overflow.

The number of baffles employed per reactor will vary depending upon the size of the reactor, and more particularly, its length. Typically, 3 or more baffles, and preferably, 6 or more baffles, are employed per reactor. Typically, less than 15 baffles, and preferably, less than 12 baffles, are employed per reactor. In an even more preferred embodiment, each baffle contains one or more weep holes that function as escape ports for excess gas build-up in the reactor. Excess gases include, for example, the diluent gas and any olefin gas exceeding the solubility limit of olefin in the liquid reaction phase, as well as oxygen, formed by side reactions. It is desirable to remove these gases from the reactor. The size of the weep holes will vary depending upon the scale of the reactor. Typically, the weep holes are sufficiently large to allow for the upflow release of excess gases that develop in the reactor, while being small enough to prevent the escape of an unacceptable quantity of liquid reaction mixture. Additionally, the weep holes should not be so large as to induce back-mixing of the liquid reaction mixture.

Since the process of this invention is exothermic, the reactor system should also comprise one or more means for heat control. Each reactor, for example, may contain an internal means for heat control, including without limitation, internal cooling coils associated with external pumps for circulating a heat exchange fluid or refrigerant. In the multi-reactor system, the heat control means may be internal to the reactor, or alternatively, may be located external to the reactors. More preferably, for example, an external heat exchanger may be situated between each pair of adjoining reactors in the plurality of sequentially interconnected reactors, as illustrated in FIG. 2 (Units 24, 34, 44, 54, 64, 74, and 84). The heat exchanger may comprise any conventional design for removing the exothermic heat of reaction, including, for example, passing the effluent product lines through a heat exchange fluid or refrigerant. Conduit lines for transporting the heat exchange fluid into and out of the heat exchangers are shown, for example, in FIG. 2 as arrows 26, 36, 46, 56, 66, 76, and 86.

Any epoxidation process conditions of temperature, pressure, and residence time can be employed in the individual reactors in the reactor system described herein, provided that the reactants are in the liquid phase and the overall process produces olefin oxide, preferably, in a selectivity of at least 90 mole percent. The epoxidation process conditions may suitably include a target temperature greater than 80° C., and preferably, greater than 100° C. The epoxidation process conditions may suitably include a target temperature less than 130° C., and preferably, less than 120° C. In a multi-reactor system, the reactors may all be maintained at a closely similar target temperature; or alternatively, the target temperature may vary from reactor to reactor within the aforementioned broad temperature range. It is not required that each reactor be maintained at strictly isothermal conditions throughout the process period. The temperature of each reactor may vary over the process period, so long as the temperature is maintained within a range that results in the formation of olefin oxide, preferably, in a selectivity of greater than 90 mole percent. Preferably, the temperature of each isothermal reactor is maintained at ±10° C. of the target reaction temperature. In contrast, the temperature in any adiabatic reactor will rise to its natural upper limit depending upon the exothermicity of the process.

The pressure throughout the total reactor system may be adjusted to any pressure sufficient to maintain a liquid phase throughout the reactor system. A small amount of gas phase, however, is allowed to remove undesirable gases, like oxygen, from the reactors. Typically, the pressure will be greater than 300 psig (2,068 kPa). Typically, the pressure will be less than 1,000 psig (6,895 kPa), and preferably, less than 850 psig (5,861 kPa). Generally, the pressure is substantially isobaric throughout the reactor system.

The residence time of the liquid phase in the total reactor system may be adjusted within a wide range, but typically depends upon the temperature of operation. Generally, as the operating temperature increases, the residence time decreases, so as to maintain an acceptable olefin oxide selectivity. Typically, the residence time of the liquid phase in the total reactor system is greater than 10 minutes, and preferably, greater than 15 minutes. Typically, the residence time of the liquid phase in the total reactor system is less than 3 hours. If a heterogeneous catalyst is employed, then the residence time may be taken to be the inverse of the weight hourly space velocity (weight of liquid phase per weight of heterogeneous catalyst per hour, or $h^{-1}$, through the reactor system.) Suitable weight hourly space velocities of the liquid phase are typically greater than 0.1 $h^{-1}$, preferably, greater than 0.2 $h^{-1}$, and typically less than 10 $h^{-1}$, preferably, less than 1.0 $h^{-1}$.

When the process of this invention is conducted as described hereinabove, then olefin, preferably propylene, and organic hydroperoxide, preferably ethylbenzene hydroperoxide, are converted to olefin oxide, propylene oxide, and the corresponding alcohol, preferably, α-phenylethyl alcohol. In the process of this invention, the conversion of organic hydroperoxide, taken as the total moles of organic hydroperoxide converted to products, is beneficially greater than 95 mole percent, preferably, greater than 96 mole percent, and more preferably, greater than 97 mole percent. The selectivity to olefin oxide, preferably propylene oxide, taken as the moles of olefin oxide produced per mole of organic hydroperoxide reacted, is beneficially greater than 90 mole percent, preferably, greater than 92 mole percent, more preferably, greater than 94 mole percent.

The invention will be further clarified by a consideration of the following examples, which are intended to be purely exemplary of the use of the invention. Other embodiments of the invention will be apparent to those skilled in the art from a consideration of this specification or practice of the invention as disclosed herein.

EXAMPLE 1

The epoxidation of propylene with ethylbenzene hydroperoxide was evaluated with a molybdenum-based catalyst in the reactor system illustrated in FIG. 2. With reference to FIG. 2, the reactor system was constructed from eight adiabatic, plug flow reactors [each 18.3 m length by 3.05 m inner diameter] (units 22, 32, 42, 52, 62, 72, 82, and 92) connected in vertical sequential series. Each reactor contained 9 baffles (shown as short horizontal lines in each reactor) to facilitate plug flow behavior. An external heat exchanger was situated between each adjoining pair of reactors for a total of 7 heat exchangers (units 24, 34, 44, 54, 64, 74, and 84; each exchanger 111.5 $m^2$; delta T per exchanger, (41.7° C.); heat transfer coefficient, 100 BTU's/h/$ft^2$). The temperature in each reactor was maintained at 111° C.±4° C. Pressure in the reactor system was essentially isobaric at 750 psig (5,171 kPa gauge). A feed stream comprising molybdenum 2-ethylhexanoate dissolved in ethylbenzene (0.02 mmol) obtained from primary feed line 10 was fed to feed line 23 at a rate of 1,990 kg/h. Propylene was fed into feed line 10 and from there to feed line 23 at a rate of 151,379 kg/h. An ethylbenzene hydroperoxide feed, provided as feed line 15 and comprising ethylbenzene hydroperoxide (25 weight percent) in ethylbenzene, was fed to ethylbenzene feed line 18, which was split into eight equal ethylbenzene hydroperoxide feeds as split feed lines 25, 35, 45, 55, 65, 75, 85, and 95. The first of the split ethylbenzene hydroperoxide feedstreams, shown as ethylbenzene hydroperoxide feed line 25, was combined with the propylene and catalyst feed from primary feed line 10 to form combined reactant feed in feed line 23, which was fed into the first reactor (unit 22). The feed rate of the total ethylbenzene hydroperoxide feed was 311,503 kg/h. The molar ratio of propylene to total ethylbenzene hydroperoxide was 5.833:1. A first effluent product stream obtained in first effluent product line 20, which comprises propylene oxide, α-ethylphenyl alcohol, acetophenone, ethylbenzene, unreacted propylene, molybdenum catalyst, and unreacted ethylbenzene hydroperoxide if any, was passed through external heat exchanger 24, equipped with heat exchange fluid in fluid line 26, and exited as heat exchanged first effluent product stream in first heat exchanged effluent product line 21. In FIG. 2, the conduit for the heat exchange fluid in heat exchanger 24 was shown as arrowed line 26. The heat exchanged first effluent product stream in product line 21 was combined with a second portion of fresh ethylbenzene hydroperoxide feed provided from second split ethylbenzene hydroperoxide feed line 35 to form a second combined feed stream in feed line 33, which enters second reactor (unit 32). A second effluent product stream as effluent product line 30 from reactor 32 was passed through an external heat exchanger 34, also equipped with heat exchange fluid from heat exchange fluid line 36, and a heat exchanged second effluent product stream was obtained therefrom as second effluent product line 31. The heat exchanged second effluent product stream from second effluent product line 31 was combined with a third fresh feed of ethylbenzene hydroperoxide provided from third split feed line 45 to form a third combined feed stream in third feed line 43, which was fed to third reactor (unit 42). A third effluent product line obtained as third effluent product line 40 from third reactor 42 was passed through an external heat exchanger 44, also equipped with heat exchange fluid in heat exchange fluid line 46, and a heat exchanged third effluent product was obtained therefrom as third effluent product line 41. The third heat exchanged effluent from third heat exchanged effluent product line 41 was combined with a fourth fresh feed of ethylbenzene hydroperoxide provided from fourth split feed line 55 to form a fourth combined feed stream as feed line 53, which enters fourth reactor (unit 52). A fourth effluent product stream from the fourth reactor obtained as fourth effluent product line 50 was passed through an external heat exchanger 54, equipped with heat exchange fluid in heat exchange fluid line 56, and a heat exchanged fourth effluent product was obtained therefrom as heat exchanged fourth effluent product line 51. Thereafter, the process was reiterated four more times, using the heat exchanged effluents from effluent product lines 51, 61, 71, and 81 comprising propylene oxide, α-ethylphenyl alcohol, acetophenone, ethylbenzene, unreacted propylene, molybdenum catalyst, and unreacted ethylbenzene hydroperoxide if any, being combined, respectively, with fresh split ethylbenzene hydroperoxide feeds from feed lines 65, 75, 85, and 95, to form reactant feeds in feed lines 63, 73, 83, and 93. The reactant feeds 63, 73, 83, and 93 were fed respectively to reactor units 62, 72, 82, and 92. Product effluents from reactor units 62, 72, and 82, obtained in product effluent lines 60, 70, and 80, were heat exchanged through heat exchange units 64, 74, and 84 to obtain heat exchanged product effluent streams in heat exchange product effluent lines 61, 71, and 81, respectively. An eighth effluent product stream comprising propylene oxide, α-phenylethyl alcohol, ethylbenzene, molybdenum catalyst, and any unreacted ethylbenzene hydroperoxide was obtained from reactor unit 92 as eighth effluent product stream 90. The overall residence time of the liquid phase in the reactor system was 149 min. The average ethylbenzene hydroperoxide conversion in each reactor was found to be 90 mole percent. The overall ethylbenzene hydroperoxide conversion was found to be 98 mole percent. The overall propylene oxide selectivity was found to be 95 mole percent. Temperature control was satisfactorily maintained throughout the run.

EXAMPLE 2

The process of Example 1 was repeated, with the exception that the reactor system was constructed from three vertically oriented, isothermal, reactors [each 18.3 m length by 3.04 m inner diameter] sequentially interconnected in series and designed with nine baffles in each reactor to facilitate plug flow behavior. In this example, the external heat exchangers of Example 1 were not employed; rather, each reactor contained internal cooling means, more specifically, cooling coils containing a liquid refrigerant, similar in design to those seen in FIG. 1. The temperature in each reactor was maintained at 111° C.±110° C. Overall pressure was essentially isobaric at 750 psig (5,171 kPa gauge). A catalyst solution comprising molybdenum naphthenate dissolved in ethylbenzene was fed to the first reactor in the reactor series at a rate of 1,990 kg/h. Propylene was fed to the first reactor at a rate of 151,379 kg/h. An ethylbenzene hydroperoxide feed comprising ethylbenzene hydroperoxide (25 weight percent) in ethylbenzene, was split into three equal fresh feeds, and each split feed was fed to one of the reactors. The total ethylbenzene hydroperoxide feed rate was 311,503 kg/h. The molar ratio of propylene to total ethylbenzene hydroperoxide was 5.833:1. The effluent from the first reactor was fed to the second reactor; the effluent from the second reactor is fed to the third reactor. The overall residence time of the liquid phase in the reactor was 111 minutes. The effluent product stream from the third reactor was analyzed with the following results. An overall propylene oxide selectivity of 94 mole percent was found at an ethylbenzene hydroperoxide overall conversion of 98 mole percent.

COMPARATIVE EXPERIMENT 1

For comparative purposes, a process of epoxidizing propylene with ethylbenzene hydroperoxide in the presence of a molybdenum-based catalyst was evaluated in a continuous stirred tank reactor (CSTR) with cooling to maintain isothermality. The CSTR operated with back-mixing, not by plug flow behavior. Ethylbenzene hydroperoxide, provided as a 25 weight percent solution in ethylbenzene, was fed to the reactor at a rate of 311,504 kg/h. Propylene was fed to the reactor at a rate of 151,379 kg/h. The propylene was dissolved in the ethylbenzene. The molar ratio of propylene to total ethylbenzene hydroperoxide was 5.833:1. Molybdenum 2-ethylhexanoate, employed as catalyst, was mixed with the other feedstreams directly before entry into the CSTR reactor. The reactor temperature was maintained at 111° C.; pressure was autogenous. The residence time of the liquid phase was 210 min. A propylene oxide selectivity of 87 mole percent was achieved with an ethylbenzene hydroperoxide conversion of 92 mole percent. When Comparative Experiment 1 was compared with Examples 1 and 2, it was seen that a higher ethylbenzene hydroperoxide conversion and a higher propylene oxide selectivity were achieved in the claimed reactor system, having staged addition and plug flow behavior (at shorter residence times and otherwise similar operating conditions), as compared with a continuous stirred tank reactor, having neither staged addition nor plug flow behavior.

EXAMPLE 3

The liquid phase epoxidation of propylene with ethylbenzene hydroperoxide in the presence of a molybdenum catalyst was evaluated in a reactor system designed for staged-addition of hydroperoxide and plug flow behavior of the liquid phase. A tubular stainless steel reactor system was constructed consisting of two reactors (50 cc each section) and feed points at the front end of each reactor. Each reactor operated essentially under plug flow. The total feed to the reactor system comprised liquefied propylene (1.91 ml/min), peroxide solution (1.823 ml/min) containing 25 weight percent ethylbenzene hydroperoxide in ethylbenzene, and catalyst solution (0.092 ml/min) containing molybdenum 2-ethylhexanoate (0.02 mmol) as active component in ethylbenzene. All of the propylene was fed to the front end of the first reactor, however, peroxide and catalyst feeds were split into two equal parts. A first part of the peroxide and catalyst feeds was mixed with the propylene and fed to the first reactor front end directly, while the second part of the peroxide and catalyst feeds was mixed and immediately added to the front end of the second reactor. The pressure in the reactor system was maintained at 56 bar (5,600 kPa). The operating temperature was maintained at 113° C. Reactor products were analyzed every 30 minutes by gas phase chromatography. A selectivity to propylene oxide was found in the range from 92.1 to 92.9 mole percent, with an average of 92.3 mole percent, as shown in Table 1. The ethylbenzene hydroperoxide conversion was 96.1 mole percent, when the reactor had achieved stable conditions.

TABLE 1

Epoxidation of Propylene with Ethylbenzene Hydroperoxide (EBHP)[a]

|  | Example 3 | Comparative CE-2 |
|---|---|---|
| EBHP Conversion (mol %) | 96.1% | 97.2% |
| Sel (mol %) Propylene Oxide | 92.3% | 85.9% |
| Sel (mol %) Propylene Glycol | 1.3% | 2.5% |
| Sel (mol %) 1-Phenylethanol | 93.50% | 89.34% |
| Sel (mol %) Acetophenone | 4.3% | 8.0% |

[a]Reactor feed: propylene (1.91 ml/min), peroxide solution (1.823 ml/min) containing 25 wt. % EBHP, catalyst solution (0.092 ml/min); 113° C.; 5,600 kPa

COMPARATIVE EXPERIMENT 2 (CE-2)

The epoxidation of propylene with ethylbenzene hydroperoxide was evaluated in the manner described in Example 3, with the exception that the hydroperoxide feed was added to the front end of the reactor rather than in staged addition. To the same two-sectional tubular stainless steel reactor system (50 cc each section) was fed a total feed comprising liquefied propylene (1.91 ml/min), peroxide solution (1.823 ml/min) with ethylbenzene hydroperoxide (24.98 weight percent) in ethylbenzene, and catalyst solution (0.092 ml/min) containing molybdenum 2-ethylhexanoate (0.02 mmol) as active component in ethylbenzene. All feeds were mixed and immediately added to the front end of the reactor. Otherwise, the reactor system was operated and analyzed under identical process conditions as used in Example 3. A selectivity to propylene oxide was found in the range from 85.5 to 86.8 mole percent, with an average of 85.9 mole percent, as shown in Table 1. The ethylbenzene hydroperoxide conversion was 97.2 mole percent, when the continuously operated reactor had achieved stable conditions. When Example 3 was compared with Comparative Experiment 2, it was seen that the staged feed addition of hydroperoxide to a reactor with plug flow pattern increases the selectivity to propylene oxide by 6.4 percent.

What is claimed is:

1. A process of preparing an olefin oxide and a co-product alcohol comprising contacting an olefin and ethylbenzene hydroperoxide in a liquid phase in the presence of a homogeneous epoxidation catalyst under process conditions sufficient to prepare the olefin oxide and the corresponding alcohol; the contacting being conducted in a multi-reactor system designed to facilitate plug flow behavior of the liquid phase by means of from 2 to less than 12 sequentially interconnected reactors, optionally, each reactor having from 3 to less than 15 baffles dividing each reactor into 4 or more reaction zones; wherein the olefin is fed to a first reactor in the multi-reactor system; the reactor system further providing for the staged addition of the ethylbenzene hydroperoxide such that a primary ethylbenzene hydroperoxide feedstream is split into a plurality of split ethylbenzene hydroperoxide feedstreams, and the split ethylbenzene hydroperoxide feedstreams are distributed among the from 2 to less than 12 sequentially interconnected reactors, and optionally, further split among the reaction zones in each reactor.

2. The process of claim 1 wherein the olefin is propylene.

3. The process of claim 1 wherein the sequentially interconnected reactors in the multi-reactor system are each individually selected from adiabatic and isothermal reactors.

4. The process of claim 3 wherein the sequentially interconnected reactors in the multi-reactor system are each individually an adiabatic reactor.

5. The process of claim 1 wherein a multi-reactor system is employed comprising greater than 2 and less than 10 sequentially interconnected reactors.

6. The process of claim 1 wherein the design for facilitating plug flow behavior comprises from 3 to 12 baffles in each reactor.

7. The process of claim 6 wherein each baffle contains one or more weep holes.

8. The process of claim 1 wherein the ratio of moles of olefin to total moles of ethylbenzene hydroperoxide fed to the multi-reactor system is greater than 4:1 and less than 15:1.

9. The process of claim 1 wherein the olefin and the ethylbenzene hydroperoxide are dissolved in an aromatic solvent.

10. The process of claim 9 wherein the aromatic solvent is ethylbenzene.

11. The process of claim 9 wherein the ethylbenzene hydroperoxide is provided in a concentration in the solvent of greater than 5 weight percent and less than 40 weight percent.

12. The process of claim 1 wherein the epoxidation catalyst is a homogeneous molybdenum-containing catalyst.

13. The process of claim 12 wherein the epoxidation catalyst is selected from molybdenum organic salts, molybdenum inorganic salts and oxides, optionally containing one or more alkali metal oxides and/or alkali metal hydroxides.

14. The process of claim 13 wherein the epoxidation catalyst is selected from molybdenum naphthenate, molybdenum 2-ethylhexanoate, and molybdenum iso-octanoate.

15. The process of claim 1 wherein the ethylbenzene hydroperoxide is provided to the process in a liquid phase, and the epoxidation catalyst and olefin are dissolved in the liquid phase.

16. The process of claim 1 wherein the process is conducted at a target temperature of greater than 80° C. and less than 130° C.

17. The process of claim 16 wherein the process is conducted in a multi-reactor system, and at a temperature controlled to ±10° C. of the target temperature for each reactor.

18. The process of claim 1 wherein the process is conducted at an overall pressure in the reactor system from greater than 300 psig (2,068 kPa) to less than 1,000 psig (6,895 kPa).

19. The process of claim 1 wherein the catalyst is provided to the process in a concentration greater than 0.0001 mole catalyst per mole ethylbenzene hydroperoxide and less than 0.0100 mole catalyst per mole ethylbenzene hydroperoxide.

20. The process of claim 1 wherein the process is conducted at a total residence time of the liquid phase from greater than $0.1\ h^{-1}$ to less than $10\ h^{-1}$.

21. The process of claim 1 wherein the process achieves an ethylbenzene hydroperoxide conversion of greater than 95 mole percent.

22. The process of claim 1 wherein the process achieves a propylene oxide selectivity of greater than 92 mole percent.

23. The process of claim 1 wherein a catalyst-containing liquid feed is split into a plurality of split catalyst feeds, and the split catalyst feeds are distributed among the reaction zones.

24. A process of preparing propylene oxide and co-product α-phenylethyl alcohol comprising contacting propylene and ethylbenzene hydroperoxide in a liquid phase in the presence of a homogeneous molybdenum epoxidation catalyst under process conditions sufficient to prepare propylene oxide and co-product α-phenyl ethyl alcohol, the contacting being conducted in a multi-reactor system designed to facilitate plug flow behavior of the liquid phase by means of from 2 to less than 12 sequentially interconnected plug flow reactors; each reactor in the multi-reactor system being divided by from 3 to less than 15 baffles into 4 or more sequentially interconnected reaction zones; each reactor in the multi-reactor system being associated with a cooling means; and wherein propylene is fed to a first reactor in the multi-reactor system; and wherein the ethylbenzene hydroperoxide feed is split into a plurality of split ethylbenzene hydroperoxide feeds, and the split ethylbenzene hydroperoxide feeds are distributed among the plurality of sequentially interconnected plug flow reactors.

25. The process of claim 24 wherein the temperature of each reactor is maintained within ±10° C. of a target temperature.

26. The process of claim 25 wherein the target temperature is greater than 80° C. and less than 130° C.

27. The process of claim 24 wherein the reactor system comprises from 2 to less than 10 sequentially-interconnected reactors, and each reactor contains from greater than 3 to less than 12 baffles to facilitate plug flow behavior of the liquid phase.

28. The process of claim 24 wherein the catalyst is selected from molybdenum naphthenate, molybdenum 2-ethylhexanoate, and molybdenum octanoate.

29. The process of claim 24 wherein a catalyst-containing liquid feed is split into a plurality of split catalyst feeds that are distributed among the reactors in the reactor system.

* * * * *